United States Patent [19]

Peterson

[11] Patent Number: 5,044,945
[45] Date of Patent: Sep. 3, 1991

[54] SLOT FOR ORTHODONTIC BRACKETS AND METHOD

[75] Inventor: Jeffrey A. Peterson, Aurora, Colo.

[73] Assignee: RMO, Inc., Denver, Colo.

[21] Appl. No.: 527,094

[22] Filed: May 22, 1990

[51] Int. Cl.$^5$ ............................................. A61C 3/00
[52] U.S. Cl. ................................................... 433/8
[58] Field of Search ..................... 433/8, 9, 10, 11, 12, 433/13, 14, 15, 16, 17

[56] References Cited

U.S. PATENT DOCUMENTS

| D. 289,329 | 4/1987 | Evans | D24/16 |
|---|---|---|---|
| D. 290,040 | 5/1987 | Kelly | D24/16 |
| D. 291,919 | 9/1987 | Reynolds | D24/10 |
| 2,701,913 | 2/1955 | Lane | 433/8 |
| 3,303,565 | 2/1967 | Newman | 433/9 |
| 3,353,271 | 11/1967 | Blechman | 433/18 |
| 3,391,461 | 7/1968 | Johnson | 433/17 |
| 3,438,132 | 4/1969 | Rubin | 433/11 |
| 3,477,128 | 11/1969 | Andrews | 433/16 |
| 3,504,438 | 4/1970 | Wittman et al. | 433/8 |
| 3,660,900 | 5/1972 | Andrews | 433/16 |
| 3,729,826 | 5/1973 | Kesling | 433/16 |
| 3,775,850 | 12/1973 | Northcutt | 433/16 |
| 3,881,252 | 5/1975 | Andrews | 433/16 |
| 3,932,940 | 1/1976 | Andren | 433/9 |
| 3,964,165 | 6/1976 | Stahl | 433/8 |
| 4,139,945 | 2/1979 | DiGiulio | 433/16 |
| 4,149,314 | 4/1979 | Nonnemann | 433/13 |
| 4,248,588 | 2/1981 | Hanson | 433/11 |
| 4,249,897 | 2/1981 | Anderson | 433/8 |
| 4,415,330 | 11/1983 | Daisley et al. | 433/16 |
| 4,443,189 | 4/1984 | Wildman | 433/10 |
| 4,531,911 | 7/1985 | Creekmore | 433/8 |
| 4,575,337 | 3/1986 | Fujita | 433/8 |
| 4,655,707 | 4/1987 | Chasanoff | 433/9 |
| 4,655,708 | 4/1987 | Fujita | 433/10 |

Primary Examiner—John J. Wilson
Attorney, Agent, or Firm—Sheridan, Ross & McIntosh

[57] ABSTRACT

An improved orthodontic bracket (44) has a slot (46) therein for receiving an archwire. The slot (46) has oppositely facing sidewalls (48 and 50) and a base (52). The base (52) has a protrusion (54) thereon thus forming a continuously curving surface including the sidewalls (48 and 50), the base (52) and the protrusion (54). An archwire placed in the slot (46) will rest upon the protrusion (54) rather than the base (52) or the sidewalls (48 and 50). Therefore, the archwire may be placed at a uniform depth regardless of the shape of the wire and stress is reduced in the slot (46).

19 Claims, 3 Drawing Sheets

SLOT FOR ORTHODONTIC BRACKETS AND METHOD

FIELD OF THE INVENTION

This invention relates in general to orthodontic devices, and in particular to an improved orthodontic bracket slot formed in the body of the bracket for reducing stress on the bracket and for uniformly positioning orthodontic wires regardless of the cross-sectional shape of the wire.

BACKGROUND OF THE INVENTION

In orthodontics, ceramics and plastics are becoming more commonly used in the formation of brackets With the increase in the use of ceramics and plastics, there is a corresponding increase in the frequency of breakage of such brackets Ceramic and plastic brackets tend to break more readily than a similarly designed metallic bracket due to a lack of ductility which is inherent in the materials used. When stress is placed on a metallic bracket, the ductile metal tends to deform or bend rather than crack or break. Contrarily, ceramics and some plastics will tend to crack or break rather than bend. When a bracket breaks due to stress from an orthodontic appliance, the broken portion results in a small jagged piece which is loose in the mouth of a patient.

In an effort to reduce the likelihood of the bracket breaking or cracking, the wire slots have been altered from a standard square or rectangular shape with orthogonally intersecting surfaces to a more rounded or smooth shaped slot. The use of such smooth shaped slots reduces the likelihood of cracks occurring at the orthogonal intersection of the surfaces Unfortunately, whenever a square or rectangularly shaped wire is used in a bracket slot that is rounded, there is an increased tendency for the wire to bind or cause excessive friction at the points of contact between the slot and the wire. Additionally, a square or rectangular shaped wire will not be correctly positioned in a rounded slot as the slot prevents full insertion of the wire which may result in some degree of misapplication of the desired adjusting forces Thus, there is a need for an orthodontic bracket slot which is shaped to take advantage of the stress reducing conditions of a rounded slot and yet allow round and square wires to be properly positioned in the slot.

SUMMARY OF THE INVENTION

The present invention disclosed herein comprises an improved slot formed in the body of the bracket which eliminates or greatly reduces problems associated with prior orthodontic slots. The present invention allows the positioning of an archwire in the slot at a uniform depth regardless of the shape of the wire while utilizing the stress reducing advantages of a curved slot.

In accordance with one aspect of the invention, an improved orthodontic bracket slot comprises first and second oppositely facing sidewalls with a base interconnecting the first and second sidewalls to form a continuously curving surface. The base has a protrusion thereon having an axial length and is positioned between the sidewalls. When an orthodontic wire is placed in the slot, the wire will rest upon the protrusion therein regardless of whether the wire is round, square or rectangular. Thus, the stress-reducing advantages of a curved slot are utilized without the mispositioning inherent between a square wire and a curved slot formed in accordance with the prior art.

BRIEF DESCRIPTION OF THE DRAWINGS

For a more complete understanding of the invention and for further advantages thereof, reference is now made to the following Detailed Description taken in conjunction with the accompanying Drawings in which.

DETAILED DESCRIPTION OF THE INVENTION

Figure 1:
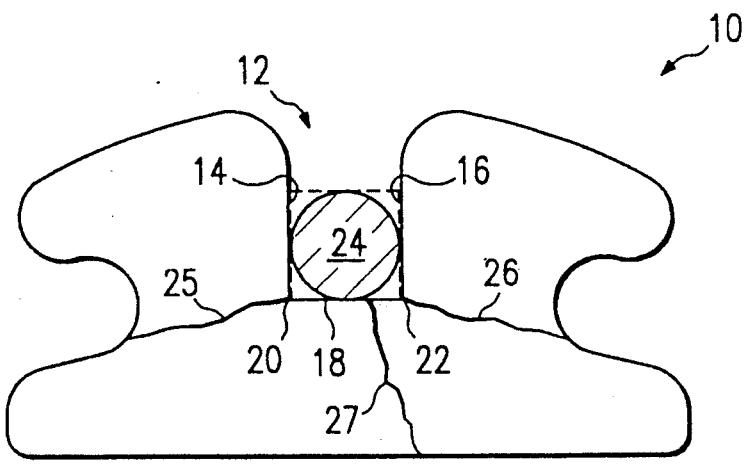
FIG. 1 is an end view of an orthodontic bracket and slot constructed in accordance with the prior art.

Referring to FIG. 1, an end view of an orthodontic bracket and slot formed in conjunction with the prior art is generally identified by the reference numeral 10. The bracket 10 has a slot 12 formed therein having parallel and oppositely facing sidewalls 14 and 16. A base 18 interconnects the sidewalls 14 and 16 generally forming right angles at the points of intersection 20 and 22. As can be seen in FIG. 1, a wire 24 having either a circular or square cross-sectional shape will be positioned in the slot 12 at approximately the same location.

If the bracket 10 comprises a ductile metal, any stress induced by the wire 24 against the bracket 10 in the slot 12 will, if severe enough, result in deformation of the bracket 10. However, if the bracket 10 comprises ceramic or plastic, stress induced by the wire 24 may cause cracks, such as indicated by the numerals 25, 26 and 27, starting at the points of intersection 20 and 22 or the base 18. If the cracks 25, 26 and 27 extend from the slot 12 to the exterior surfaces of the bracket 10, small jagged pieces may break from the bracket 10 and become hazardous objects in the mouth. Additionally, any jagged edges left on the bracket 10 from breakage thereof, will also cause potential hazards to the patient.

Figure 2:
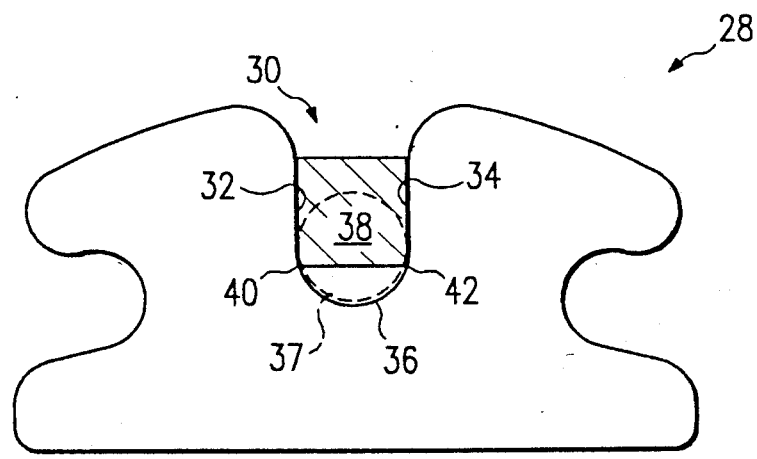
FIG. 2 is an end view of another orthodontic bracket and slot also constructed in accordance with the prior art.

Referring to FIG. 2, another bracket constructed in accordance with the prior art is generally identified by the reference numeral 28. The bracket 28 has a slot 30 formed therein with generally parallel sidewalls 32 and 34. A base 36 interconnects the sidewalls 32 and 34 forming a continuously curved slot for receiving a round archwire 37. The slot 30 thus eliminates or greatly reduces the sharp points of intersection (points 20 and 22 of FIG. 1) of a rectangular slot. Thus, the tendency for cracks to occur along the points of intersection between the base and the sidewalls is greatly reduced.

However, if an archwire 38 with a square or rectangular cross section is positioned in the slot 30, there will be contact between the archwire 38 and the slot 30 as indicated by the reference numerals 40 and 42. At the points of contact 40 and 42 there is a tendency for binding between the archwire 38 and the bracket 28 as well as frictional forces therebetween. Additionally, due to the shape of the archwire 38, the archwire 38 may not be positioned completely within the slot 30, as opposed to a round archwire which would be seated on the base 36. As a result, there will be a difference in the positioning and therefore a difference in the application of forces between a square wire and a round wire. Thus, while the slot 30 greatly reduces the tendency of cracking as opposed to a rectangular slot, there are positioning and force disadvantages inherent thereto.

Figure 3:
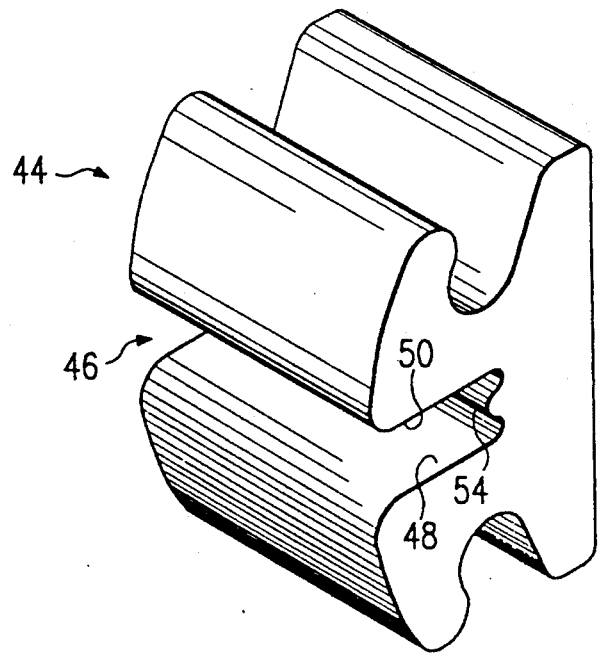
FIG. 3 is an isometric view of a bracket and slot constructed in accordance with the preferred embodiment of the present invention.

Referring to FIG. 3, a bracket 44 including a body with a slot formed in accordance with the preferred embodiment of the present invention, generally identified by the reference numeral 46, is shown in perspective. The bracket 44 is of a standard shape well known in the art and may comprise ceramic, plastic, composite or metal which is formed by any appropriate method such as molding, stamping or die cutting. The slot 46 passes through the bracket 44 along a longitudinal axis thereof. A protrusion 54 is formed in the slot 46 to support an archwire placed therein, as will be subsequently described in greater detail.

Figure 4:
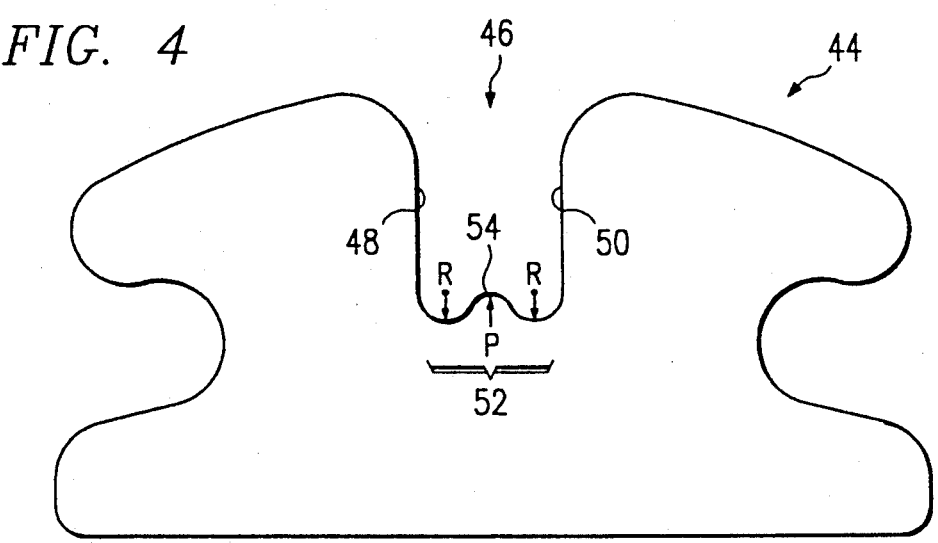
FIG. 4 is an end view of the orthodontic bracket of FIG. 3.

Referring to FIG. 4, the bracket 44 of FIG. 3 is shown in an end view. The slot 46 is formed with oppositely facing sidewalls 48 and 50. A base 52 interconnects the sidewalls 48 and 50 in order to form a continuously curved slot in conjunction with the protrusion 54.

The protrusion 54 has a shape generally opposite to the curve formed between the base 52 and the sidewalls 48 and 50. In the preferred embodiment, the continuously curving surface formed by the base 52 and the protrusion 54 resembles a uniform wave (such as a sine wave) defined by a radius R forming a curve which meets with a tangent to a similar but reverse curve having a radius P. Thus, the slot 46 has no stress concentration points formed by sharply intersecting portions thereof. The slot 46 will therefore have the advantage of the reduced stress points of rounded or curved slots as formed in the prior art (see FIG. 2) but will not have the archwire positioning problems thereof.

Figure 5:
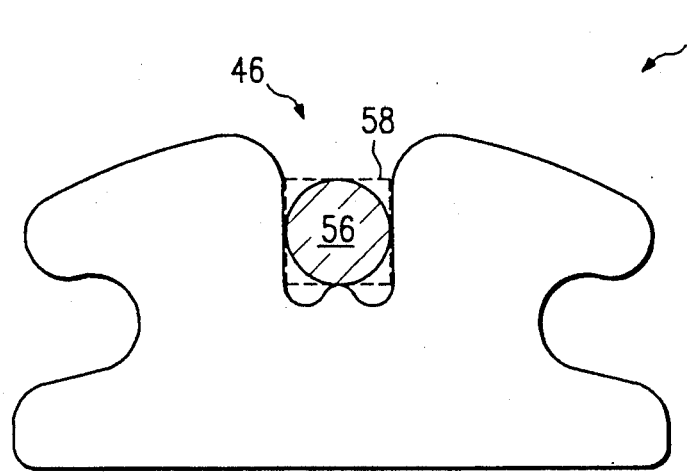
FIG. 5 is an end view of the bracket of FIG. 3 with orthodontic wires positioned in the slot.

Referring to FIG. 5, the bracket 44 and slot 46 are shown with a cross-sectionally square wire 58 superimposed on a cross-sectionally round wire 56. It can be seen in FIG. 5 that, regardless of the cross-sectional shape of the archwire, the wire will be positioned at the same depth within the slot 46. Additionally, when the square wire 56 is used in the slot 46, there will be no excess binding or friction as experienced with a square wire in a curved slot in accordance with the prior art (see FIG. 2). It is to be understood that the wire 56 or 58 will be at least slightly smaller than the width of the slot 46 to ensure easy insertion thereof.

Figure 6:
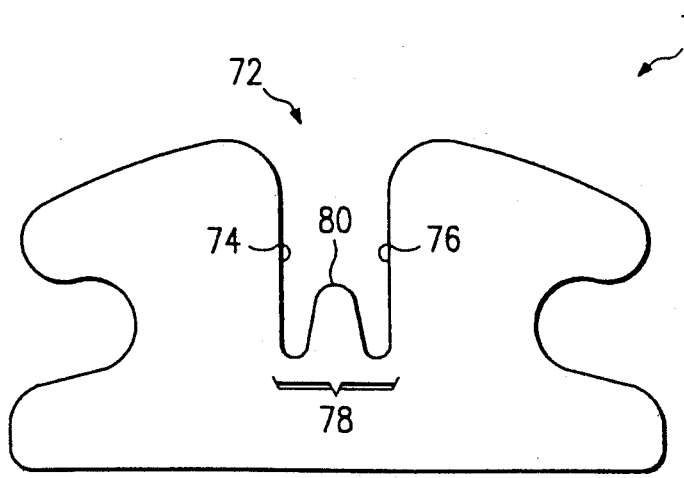
FIGS. 6-9 are alternative embodiments of a slot formed in conjunction with the present invention.

Referring to FIG. 6, one alternative embodiment of the present invention is shown. A bracket 70 has a slot 72 formed therein. The slot 72 comprises oppositely facing sidewalls 74 and 76 joined by a base 78. The base 78 has a protrusion 80 forming a continuously curving slot in conjunction with the base 78 and the sidewalls 74 and 76. The protrusion 80 can be any appropriate shape such as hyperbolic, parabolic, elliptical or etc. that forms a continuously curving slot. Although not shown, it is also to be understood that the protrusion, such as protrusions 54 and 80, do not have to be centered between the slot sidewalls nor of a uniform shape.

Figure 7:
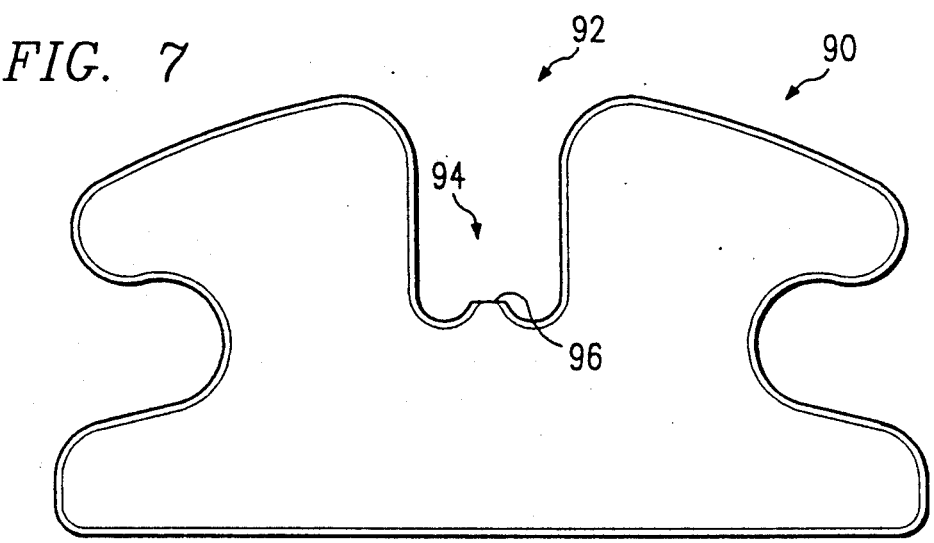
Figure 8:
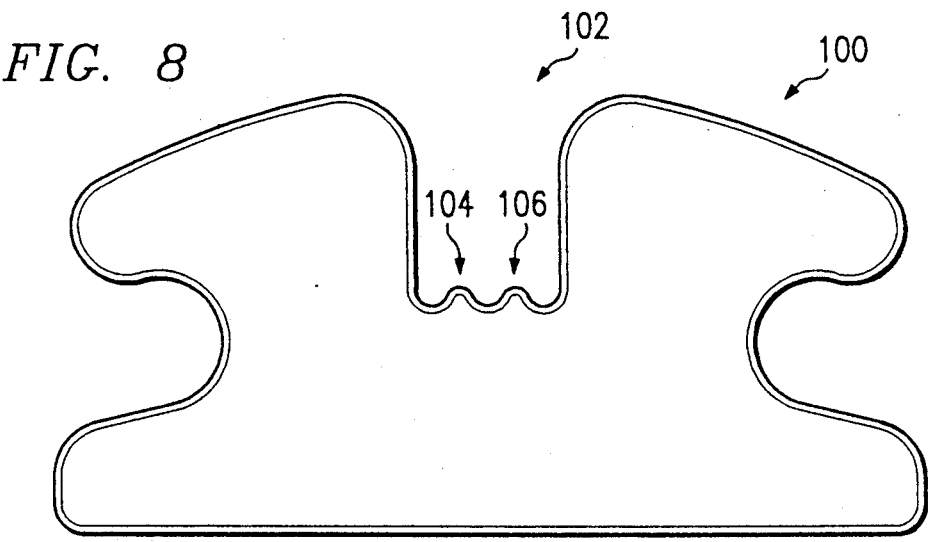
Figure 9:
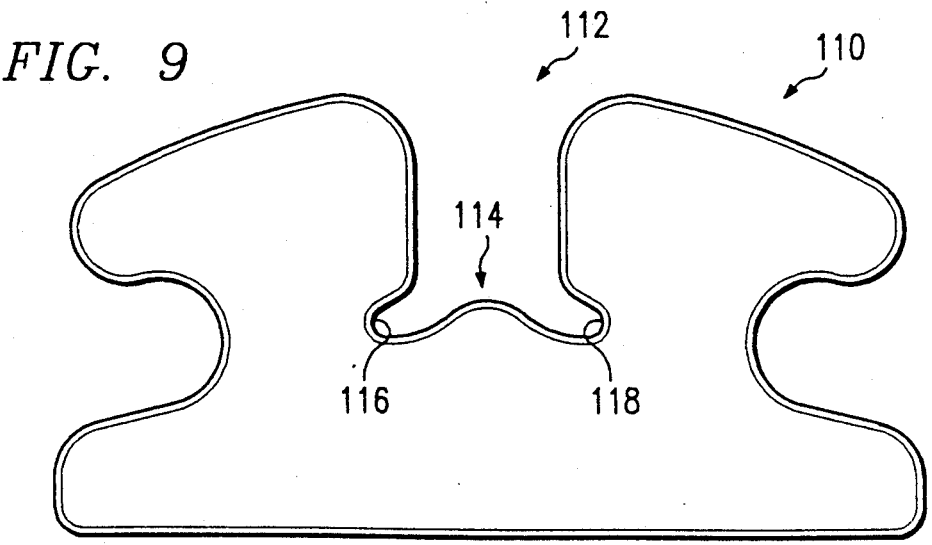

Referring to FIGS. 7, 8 and 9, further alternative embodiments are shown. Referring first to FIG. 7, a bracket 90 is formed with a slot 92 and a protrusion 94 having a generally planar top surface 96. The remaining surfaces of slot 92 are curved as previously described above. Referring to FIG. 8, a bracket 100 is formed with a slot 102 and a plurality of protrusions such as protrusions 104 and 106. The protrusions 104 and 106 should be spaced and sized appropriately in order to allow an archwire o any shape to rest thereupon at a uniform depth within the slot 102.

Referring to FIG. 9, a bracket 110 is formed with a slot 112 therein. The slot 112 is continuously curving with a protrusion 114 but further includes undercuts 116 and 118. The undercuts 116 and 118 serve to provide a greater area for stress reduction in the slot 112. It is important in the present invention to provide a slot with any combination of curved and/or planar surfaces that eliminates the likely stress concentration points formed by sharply intersecting portions thereof. It is to be understood that there is no requirement for the curving surfaces to be uniform or to meet at tangents thereto.

Thus it can be seen that the present invention offers a particular advantage over the prior art by eliminating or greatly reducing the problems associated therewith. By providing a slot that eliminates the stress points formed at the intersection between oblique surfaces, the present invention greatly reduces the likelihood of bracket breakage. The protrusion along the base of the slot also helps allow wires of any shape to be uniformly positioned for the predictable application of force to the teeth.

Although the present invention has been described with respect to its specific preferred embodiment thereof, various changes and modifications may be suggested to one skilled in the art, and it is intended that the present invention encompass such changes and modifications as fall within the scope of the appended claims.

What is claimed is:

1. An orthodontic bracket, comprising:
    a body having a slot defined by sidewalls and a base formed in said body for receiving an orthodontic wire; and
    means for reducing frictional and binding contact between said slot and the orthodontic wire, wherein said means for reducing includes a protrusion formed on said base between said sidewalls, said protrusion being spaced from said sidewalls and ending before said base merges with said sidewalls, and further comprises curving surfaces adjacent to said sidewalls with a planar top surface therebetween.

2. An orthodontic appliance, comprising:
    an orthodontic wire;
    a bracket having a slot defined by sidewalls and a base formed in said bracket for receiving said wire; and
    a protrusion in said base for reducing frictional and binding contact between said slot and said wire, said protrusion being spaced from said sidewalls and ending before said base merges with said sidewalls and wherein said protrusion substantially continuously contacts said orthodontic wire along substantially the entire length of that portion of said orthodontic wire that is positioned in said slot.

3. The bracket of claim 2, wherein said protrusion comprises:
    a continuously curving surface adjacent to said base and said sidewalls.

4. The bracket of claim 2, wherein said protrusion comprises:
    curving surfaces adjacent to said sidewalls with a planar top surface therebetween.

5. An improved orthodontic bracket slot, comprising:
first and second oppositely facing sidewalls;
a base interconnecting said first and second sidewalls, said base having an axial length; and
a protrusion between said sidewalls provided on at least a portion of said axial length of said base, wherein a continuously curving surface is formed by said sidewalls, said base and said protrusion.

6. The slot of claim 5, wherein said continuously curving surface comprises:
a uniform wave.

7. The slot of claim. 5, wherein said protrusion comprises:
a semicircle.

8. The slot of claim 5, wherein said protrusion comprises:
a hyperbola.

9. The slot of claim 5, wherein said protrusion comprises:
a parabola.

10. The slot of claim 5, wherein said protrusion comprises:
an ellipse.

11. The slot of claim 5, wherein said protrusion further comprises:
curved undercuts adjacent said base and each of said oppositely facing sidewalls.

12. An improved orthodontic bracket, wherein the improvement comprises:
a slot having sidewalls and a base which merge to form a continuously curving surface; and
a raised portion along said base of said slot merging with said continuously curving surface to form a wave.

13. The bracket of claim 12, wherein said raised portion comprises:
a semicircle.

14. The bracket of claim 12, wherein said wave comprises:
a first curve having a first radius;
a second curve having a second and opposite radius, wherein a tangent from said first curve merges with a tangent from said second curve; and
a third curve having a third radius equal to said first radius, wherein a tangent from said second curve merges with a tangent from said third curve.

15. A method for reducing friction between an orthodontic bracket and an arch wire, comprising the steps of:
forming a slot adjacent to sidewalls of the bracket to receive th arch wire; and
forming a protrusion on a base defining said slot, said protrusion being spaced from said sidewalls and ending before said base merges with said sidewalls, in order to allow the wire to rest upon said protrusion when placed in said slot, wherein frictional contact between the bracket and the wire is reduced.

16. The method of claim 15, wherein the step of forming a protrusion comprises:
merging a tangent of said protrusion with equal but opposite tangents from curves formed by said base and said sidewalls of said slot.

17. The method of claim 15, further comprising the step of:
accurately merging said sidewalls with said base and said protrusion with said base.

18. The method of claim 15, further comprising the step of:
undercutting said sidewalls adjacent said base.

19. A method for reducing binding and frictional contact between an orthodontic wire and a bracket slot, comprising the steps of:
forming a protrusion on a base of the slot, said protrusion spaced from side walls of the slot and ending before said base merges with said sidewalls; and
positioning the wire in the slot in order that said protrusion substantially continuously contacts the wire along substantially the entire length of that portion of the orthodontic wire that is positioned in the slot, wherein contact between the wire and the slot is lessened thereby reducing binding and friction therebetween.

* * * * *